US00PP34482P2

(12) United States Plant Patent
Bourne

(10) Patent No.: US PP34,482 P2
(45) Date of Patent: Aug. 9, 2022

(54) GRAPEVINE NAMED 'SV33-101-337'

(50) Latin Name: ***Vitis vinifera* L.**
Varietal Denomination: 'SV33-101-337'

(71) Applicant: Sunview Vineyards of California, Inc., Delano, CA (US)

(72) Inventor: Timothy F Bourne, Visalia, CA (US)

(73) Assignee: Sunview Vineyards of California, Inc., Delano, CA (US)

( * ) Notice: Subject to any disclaimer, the term of this patent is extended or adjusted under 35 U.S.C. 154(b) by 0 days.

(21) Appl. No.: 17/803,139

(22) Filed: Mar. 1, 2022

(51) Int. Cl.
*A01H 6/88* (2018.01)
*A01H 5/08* (2018.01)

(52) U.S. Cl.
USPC ..... Plt./205

(58) Field of Classification Search
USPC ..... Plt./205
See application file for complete search history.

*Primary Examiner* — Annette H Para
(74) *Attorney, Agent, or Firm* — Eric C. Cole; Baker Manock & Jensen, PC

(57) ABSTRACT

A new and distinct variety of grapevine plant named 'SV33-101-337' particularly characterized by its sweet, crisp red berries which ripen in late July and early August in the McFarland, Calif. area.

3 Drawing Sheets

Latin name of the genus and species of the plant claimed: The plant claimed relates to a new and distinct variety of *Vitis vinifera* L.

Variety denomination: The plant claimed shall be known as 'SV33-101-337'.

STATEMENT OF ANY FEDERALLY-SPONSORED RESEARCH AND DEVELOPMENT

The present invention is not subject of Federally-sponsored research or development.

BACKGROUND OF THE INVENTION

The present invention comprises a new and distinct cultivar of grapevine botanically known as *Vitis vinifera* L. and hereinafter referred to as grapevine named 'SV 33-101-337'. As used herein, 'grapevine' refers to all plant parts including vines, shoots, canes, tendrils, leaves, fruit and roots of 'SV33-101-337'. Grapevine named 'SV33-101-337' is the result of an effort to produce an early ripening, red, seedless table grape with fruit characteristics and productivity superior to currently available red, seedless cultivar 'Flame Seedless' (unpatented). This new cultivar originated from a cross conducted in May 2012 near McFarland, Calif. between female parent grapevine selection 'SV24-28-356' (unpatented) and male parent grapevine selection 'SV30-25-602' (unpatented). Resultant ovules from the cross were harvested 42 days after pollination and cultured on 'McCown's Woody Plant Medium'. Subsequently, the resultant embryonic plants were cultured in the same medium in the laboratory under twelve hours of light from standard fluorescent lamps at 29° C. The seedlings from this effort were transplanted to the greenhouse in October of 2012 and grown in the greenhouse at 29° C. with 12 hours illumination under high pressure sodium vapor lamps. The seedling population of 63 plants was planted in the field in the spring of 2013 near Delano, Calif. The new grapevine was selected from this seedling population on Jun. 23, 2015. It was then propagated by cuttings and grafted to 'Freedom' (unpatented) rootstock in 2016. The resultant vines were planted in a trial near McFarland, Calif. in May of 2016 and were trained to a t-trellis on 2.1 meter by 3 meter spacing. The present invention has been found to retain its distinctive characteristics through two successive asexual propagations.

Grapevine named 'SV33-101-337' differs from its female parent grapevine named 'SV24-28-356' in that 'SV33-101-337' has berries with well-sealed tips which are resistant to decay on the vine while 'SV24-28-356' has poorly sealed berry tips which have some tendency to decay prior to harvest Grapevine named 'SV33-101-337' differs from its male parent grapevine named 'SV30-25-602' in that 'SV33-101-337' has red berries while 'SV30-25-602' produces berries which are green.

Grapevine named '33-101-337' most closely resembles commercially available cultivar 'Flame Seedless' (unpatented) but differs from it in that grapevine '33-101-337' produces berries which are well sealed with no tendency to decay on the vine while 'Flame Seedless' (unpatented) produces berries which have poorly sealed tips with some tendency to split causing decay prior to harvest in some seasons.

SUMMARY OF THE INVENTION

The following are the most outstanding and distinguishing characteristics of this new variety when grown under normal horticultural practices near McFarland, Calif.:

1. Bright red to dark red-purple berries with well-sealed tips which have no tendency to split causing berry decay.
2. Very firm berry texture; and
3. Medium-sized, sweet berries with neutral flavor which ripen in early mid-season near McFarland, Calif.

BRIEF DESCRIPTION OF THE DRAWINGS

This new grapevine is illustrated by the accompanying photographs which show fruit clusters, leaves, canes, and tendrils. The colors shown are as true as can be reasonably obtained by conventional photographic procedures. The photographs were taken from plants about 5 years old grown near McFarland, Calif. in 2020 and 2021.

DETAILED BOTANICAL DESCRIPTION

Figure 1:
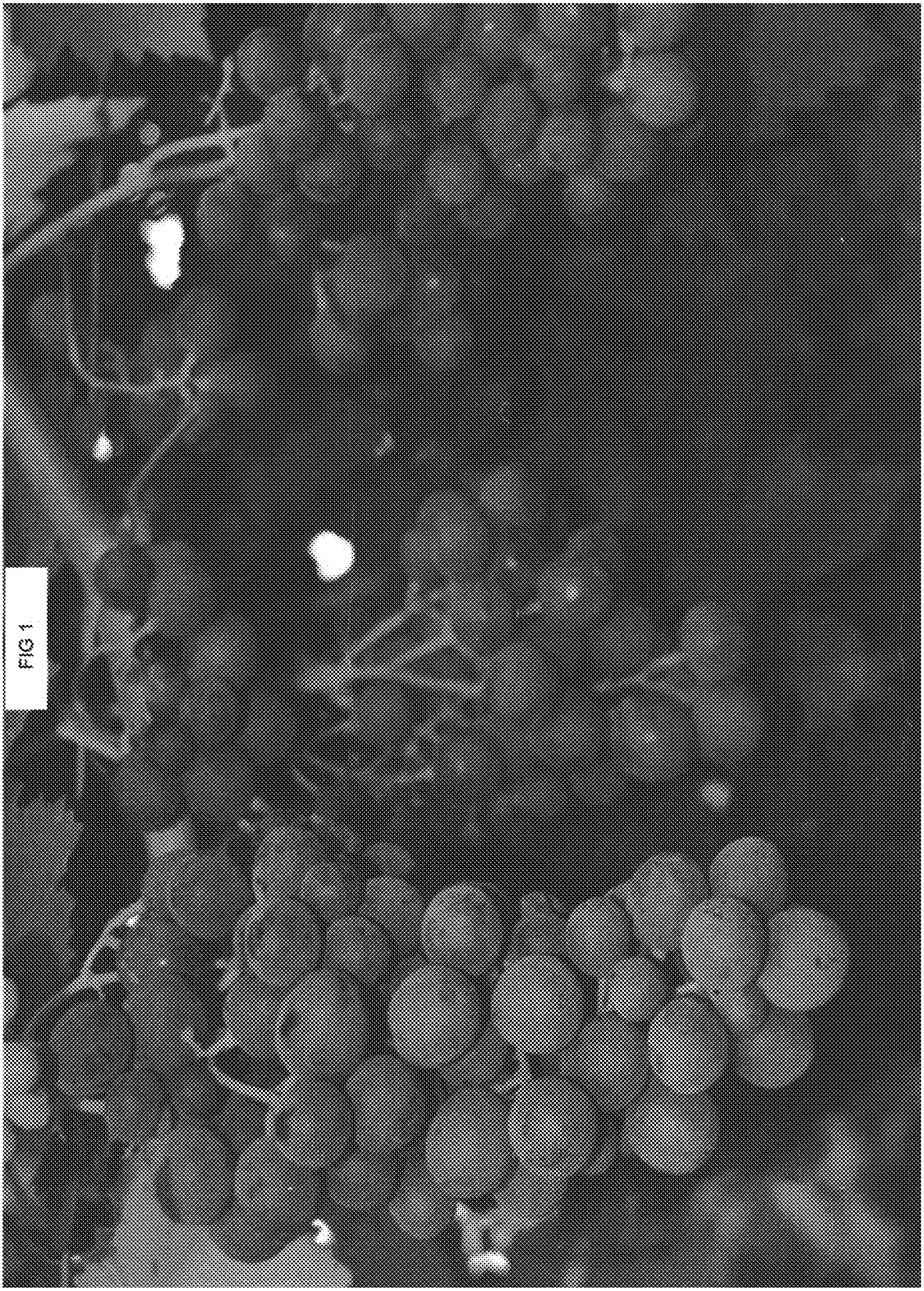
FIG. 1 Fruit clusters on seedling vine at time of selection.
Figure 2:
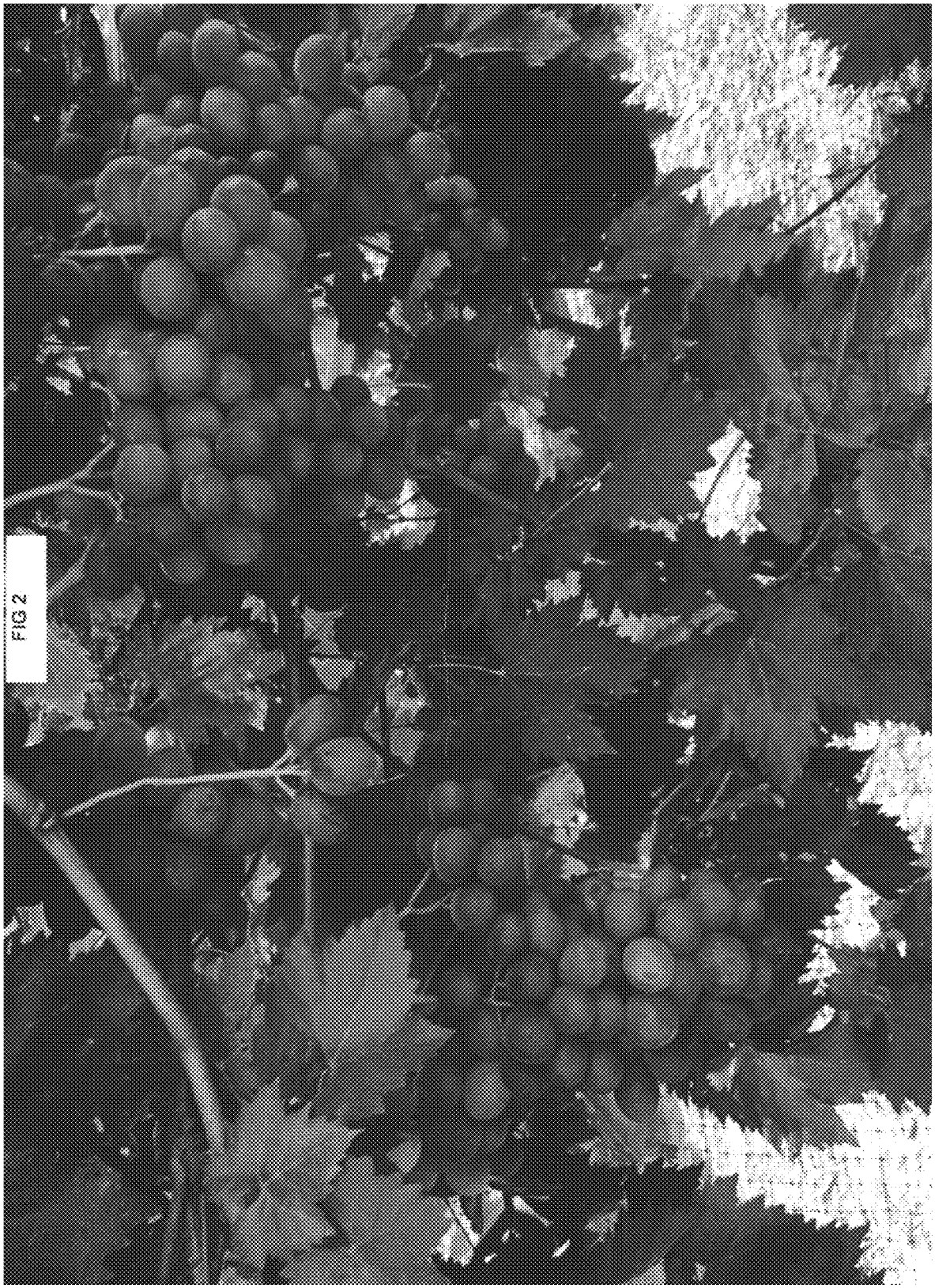
FIG. 2 Vine and clusters treated with exogenous gibberellic acid and trunk girdling.
Figure 3:
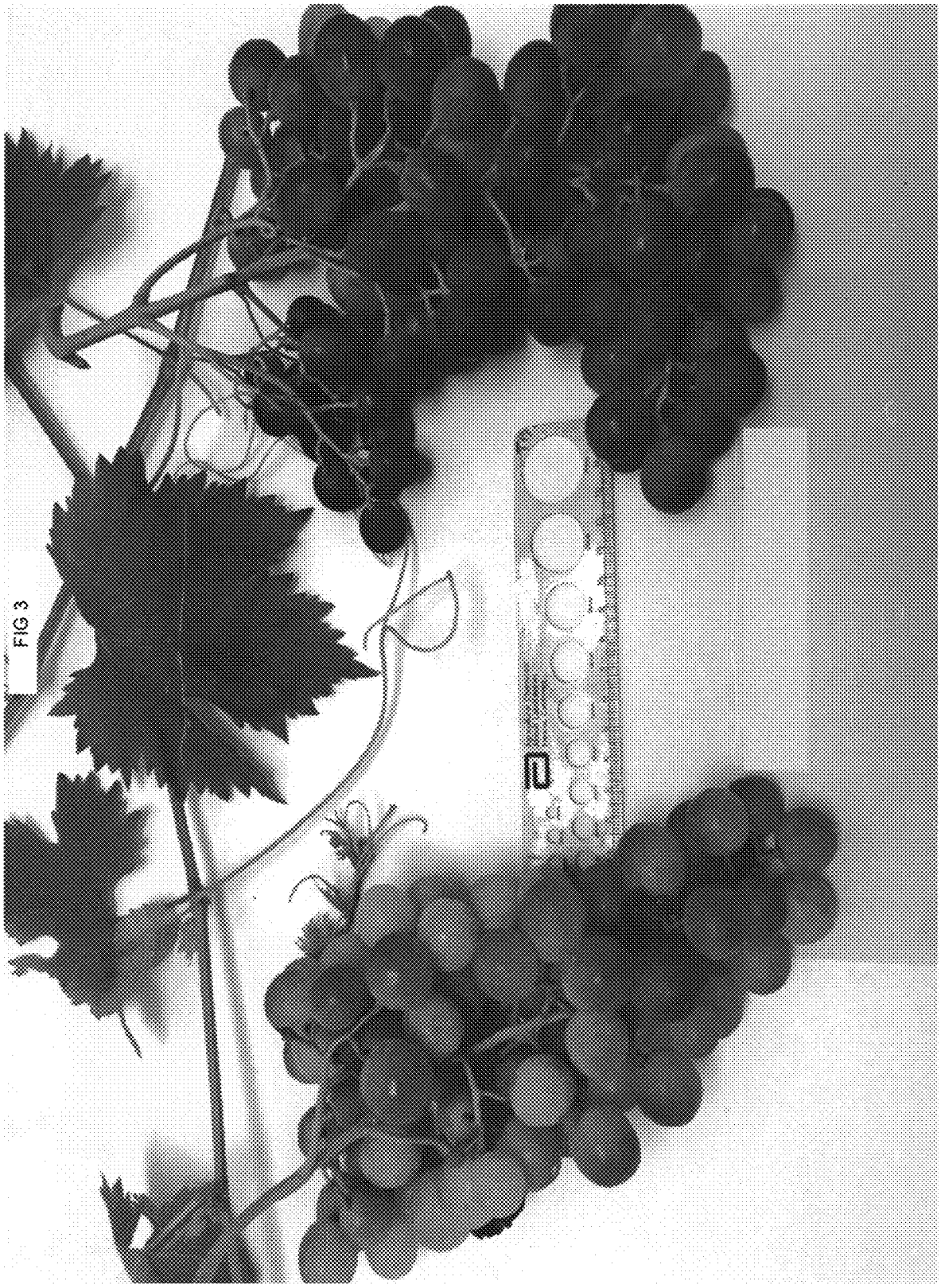
FIG. 3 Natural fruit cluster (left), fruit cluster treated with gibberellic acid (right), shoots, leaves and tendrils.

The following detailed description sets forth the distinctive characteristics of grapevine named 'SV33-101-337'. Descriptions of the new invention apply to vines of 'SV33-101-337' grown on 'Freedom' (unpatented) rootstock at a density of 1,537 vines per hectare grown near McFarland, Calif. in 2021. These vines were in their fifth year of full production having been planted in 2016. These descriptions are believed to apply generally to the new variety grown under similar circumstances elsewhere. Variation due to soil and climatic conditions in other locations may be seen. References to color primarily correspond to The Royal Horticultural Society's Colour Chart, The Royal Horticultural Society, London, United Kingdom (copyright 2001). Descriptors used herein conform to those set forth by the International Board for Plant Genetic Resources Institute Grape Descriptors (*Vitis* spp.) of 1983 and/or 1997 which were developed in collaboration with the Office International de la Vigne et du Vin (OIV) and the International Union for the Protection of New Varieties of Plants (UPOV) and published in *Descriptors for Grapevine* (*Vitis spp.*) (Anonymous, International Plant Genetic Resources Institute, 1997, ISBN 92-9043-352-3).

Classification:

- *Family*.—Vitaceac.
- *Botanical name*.—*Vitis vinifera* L.
- *Variety name*.—'SV33-101-337'.

Trunk:

- *Shape*.—Broadly elliptical.
- *Straps*.—Long, split.
- *Surface texture*.—Shaggy.
- *Trunk circumference*.—20.8 cm at 1.0 m of height.
- *Inner bark color*.—RHS Greyed Orange Group 173A.
- *Outer bark color*.—RHS Grey Group 201A.

Mature leaves:

- *Average blade length*.—16.4 cm.
- *Average blade width*.—18.8 cm.
- *Size of blade*.—Large.
- *Shape*.—Pentagonal.
- *Number of lobes*.—5.
- *Anthocyanin coloration of main veins on the upper side of the blade*.—Absent.
- *Mature leaf profile*.—Cupped upwards around entire margin.
- *Blistering* (*upper surface*).—Absent.
- *Leaf blade tip*.—In plane of blade.
- *Margins*.—Lobed, serrated, undulating.
- *Apex*.—Narrowly acuminate.
- *Bases*.—Sagittate.
- *Thickness*.—Medium.
- *Undulation of blade between main and lateral veins*.—Slight.
- *Shape of teeth*.—Broadly conical, both sides convex.
- *Length of teeth*.—3 mm to 13 mm.
- *Ratio length/width of teeth*.—About 1:1.
- *General shape of petiole sinus*.—Wide open.
- *Tooth at petiole sinus*.—Absent.
- *Petiole sinus limited by veins*.—Absent.
- *Shape of upper lateral sinus*.—Closed.
- *Depth of upper lateral sinus*.—Shallow.
- *Prostrate hairs between veins* (*lower surface*).—Absent.
- *Erect hairs between veins* (*lower surface*).—Absent.
- *Prostrate hairs on main veins* (*lower surface*).—Absent.
- *Density of erect hairs on main veins* (*lower surface*).—Sparse; limited to junctions of major veins.
- *Prostrate hairs on main veins* (*upper surface*).—Absent.
- *Upper surface*.—Summer color: RHS Green Group 139A. Surface texture: Smooth. Surface appearance: Smooth. Goffering of blade: Absent.
- *Lower surface*.—Summer color: RHS Yellow Green Group 146B. Anthocyanin coloration of main veins on lower leaf surface: Absent. Anthocyanin coloration on laterals: Absent. Glossiness: Low. Pubescence distal portion of surface: Absent. Surface texture: Rough. Surface appearance: Dull.
- *Petiole*.—Length: 12.5 cm. Length of petiole compared to middle vein: Much shorter. Density of prostrate hairs: Absent. Density of erect hairs: Absent. Color: In shade: RHS Yellow Green Group 144C. In sun: RHS Red Purple Group 59B.

Tendrils:

- *Number*.—Bifurcated and trifurcated; forming irregularly above node 5.
- *Length*.—25.2 cm.
- *Diameter*.—2.8 mm.
- *Texture*.—Smooth.
- *Color*.—RHS Yellow Green Group 144A.

Growing tips:

- *Color*.—RHS Yellow Green Group 144B.
- *Anthocyanins*.—Absent.
- *Shape*.—Rounded.
- *Apex*.—Fully open.
- *Prostrate hair on tips*.—Sparse.
- *Anthocyanin coloration of prostrate hairs on tips*.—Absent.
- *Erect hairs on tip*.—Absent.

Green summer shoots:

- *Shoot attitude*.—Semi-erect.
- *Color of dorsal side of internode*.—Red Purple Group 59B.
- *Color of ventral side of internode*.—Yellow Green Group 144B.
- *Color of doral side of nodes*.—Both red and green — Yellow Green Group 144B and Red Purple Group 59B.
- *Color of ventral side of nodes*.—Yellow Green Group 144B.
- *Erect hairs on internodes*.—Absent.

Woody shoot:

- *Canes*.—Length: 1.7 m. Shape: Broadly elliptical. Internode length: About 12.7 cm. Width at node: 10.2 mm. Cross section: Elliptic. Surface: Smooth. Main color: RHS Greyed Orange Group 166C. Lenticels: Inconspicuous.
- *Buds*.—Shape: Rounded to slightly pointed. Cane bud fruitfulness: Basal buds fruitful, usually 1-2 clusters per shoot. Length: 10 mm. Width: 7 mm. Height: 6 mm. Color: RHS Greyed Orange Group 175A.

Flowers:

*Flower type*.—Perfect.

*Position of first flowering nodes*.—Third or fourth node.

*Number of inflorescences per shoot*.—Usually 1 or 2.

*Calyptra color*.—RHS Yellow Green Group 144A.

*Ovary length*.—2.5 mm.

*Ovary width*.—1 mm.

*Ovary color*.—RHS Yellow Green Group 144A.

*Filament length*.—3 mm.

*Filament color*.—Translucent, absence of pigmentation.

*Anther length*.—0.5 mm.

*Anther color*.—RHS Yellow Group 8B.

*Date of full bloom*.—May 5, 2021.

Fruit:

*Ripening period*.—Early; first harvest in late July to early August at McFarland, Calif.

*Date of ripening*.—Aug. 3, 2022 McFarland, Calif.

*Use*.—Fresh market.

*Keeping quality*.—Very good.

*Shipping quality*.—Good.

*Solids-sugar*.—High, about 20 brix at full maturity.

*Refractometer test*.—18 brix.

*Titratable acidity*.—0.36.

*pH*.—3.88.

*Bunch*.—Size: Medium. Length (peduncle excluded): About 21.2 cm. Width: About 13.8 cm. Weight: Natural, without gibberellic acid treatment: 518.0 g. With gibberellic acid treatment: 621 g. Density: Well-filled, but loose. Number of berries per bunch: 93.6. Form: Conical, shouldered.

*Peduncle*.—Length: About 5.5 cm. Lignification: Slight. Color: RHS Yellow Green Group 144A.

*Berry*.—Size: Medium. Uniformity of size: Uniform. Mass Natural, without gibberellic acid treatment: 5.5 g. With gibberellic acid treatment: 6.2 g. Shape: Natural, without gibberellic acid treatment: Elliptic. With gibberellic acid treatment: Elliptic. Presence of seeds: Seedless; most berries develop one or two small, soft. rudimentary seeds about 0.5 mm in length. Cross section: Circular. Dimensions: Longitudinal axis: About 2.3 cm at base. Horizontal axis: About 2.1 cm. Skin color (without bloom): RHS Red group 53A to RHS Red Purple Group 63A. Coloration of flesh: Translucent; absence of pigment. Juiciness of flesh: Very juicy. Berry firmness: Very firm. Particular flavor: Neutral, typical *Vitis vinifera*. Bloom (cuticular wax): Strong. Pedicel length: 1.6 cm. Berry separation from pedicel: With difficulty.

*Skin*.—Thickness: Medium. Texture: Crisp. Reticulation: Absent. Roughness: Absent. Tenacity: Tenacious to flesh. Tendency to crack: Resistant.

Disease and insect resistance: Typical of most *Vitis vinifera* table grapes; no particular susceptibility or resistance observed. Normal disease and insect control practices may be used.

Having thus described and illustrated our new variety of grapevine, I claim:

1. A new and distinct variety of grapevine plant named 'SV33-101-337', substantially as illustrated and described herein.

* * * * *